nt Number: 6,011,161

United States Patent [19]

Kameswaran

[11] Patent Number: 6,011,161
[45] Date of Patent: Jan. 4, 2000

[54] PROCESS FOR THE PREPARATION OF 2-ARYL-5-(PERFLUOROALKYL)PYRROLE COMPOUNDS FROM N-(PERFLUORO-ALKYLMETHYL)ARYLIMIDOYL CHLORIDE COMPOUNDS

[75] Inventor: Venkataraman Kameswaran, Trenton, N.J.

[73] Assignee: American Cyanamid Company, Madison, N.J.

[21] Appl. No.: 09/246,983

[22] Filed: Feb. 9, 1999

Related U.S. Application Data

[60] Provisional application No. 60/074,098, Feb. 9, 1998.

[51] Int. Cl.$^7$ .................... C07D 207/325; C07D 207/34; C07D 207/36; C07D 207/42
[52] U.S. Cl. .................. 548/560; 548/517; 548/527; 548/531; 548/556; 548/557; 548/562; 549/68; 549/74; 549/75; 549/472; 549/481; 549/491; 558/411
[58] Field of Search ..................... 548/560, 562, 548/517, 531, 556, 557

[56] References Cited

U.S. PATENT DOCUMENTS

| | | | |
|---|---|---|---|
| 5,010,098 | 4/1991 | Brown et al. | 514/426 |
| 5,068,390 | 11/1991 | Kuhn et al. | 558/461 |
| 5,145,986 | 9/1992 | Kameswaran | 548/531 |
| 5,359,090 | 10/1994 | Doehner et al. | 548/561 |
| 5,426,225 | 6/1995 | Kameswaran | 564/212 |
| 5,446,170 | 8/1995 | Kameswaran | 548/517 |
| 5,449,789 | 9/1995 | Kameswaran | 548/561 |
| 5,817,834 | 10/1998 | Kameswaran | 548/561 |

OTHER PUBLICATIONS

K. Tanaka et al, Chemistry Letters, pp. 1463–1464 (1983).

*Primary Examiner*—Joseph K. McKane
*Assistant Examiner*—Jane Oswecki
*Attorney, Agent, or Firm*—John W. Hogan, Jr.

[57] ABSTRACT

There is provided a process for the preparation of 2-aryl-5-(perfluoroalkyl)pyrrole compounds from N-(perfluoroalkylmethyl)arylimidoyl chloride compounds. The 2-aryl-5-(perfluoroalkyl)pyrrole compounds are useful for the control of insect and acarid pests, and may also be used to prepare other pesticidal arylpyrrole compounds.

In addition, the present invention provides N-(perfluoroalkylmethyl)arylimidoyl chloride compounds which are useful as intermediates in the preparation of arylpyrrole compounds.

4 Claims, No Drawings

PROCESS FOR THE PREPARATION OF 2-ARYL-5-(PERFLUOROALKYL)PYRROLE COMPOUNDS FROM N-(PERFLUORO-ALKYLMETHYL)ARYLIMIDOYL CHLORIDE COMPOUNDS

This application claims the benefit of Provisional Application Ser. No. 60/074,098 filed Feb. 9, 1998.

BACKGROUND OF THE INVENTION

2-Aryl-5-(perfluoroalkyl)pyrrole compounds are useful as insecticidal and acaricidal agents. In addition, those compounds are also useful for the preparation of other insecticidal and acaricidal agents. In particular, 2-aryl-5-(perfluoroalkyl)pyrrole compounds are key intermediates in the preparation of arylpyrrole compounds such as chlorfenapyr. Accordingly, there is an ongoing search to discover new and more efficient methods for the preparation of 2-aryl-5-(perfluoralkyl)pyrrole compounds.

U.S. Pat. No. 5,145,986 discloses that 2-aryl-5-(trifluoromethyl)pyrrole compounds may be prepared from N-(substituted benzyl)-2,2,2-trifluoroacetimidoyl chloride compounds. However, certain 2-aryl-5-(perfluoroalkyl) pyrrole compounds may not be as readily prepared from commercially available starting materials using the process of U.S. Pat. No. 5,145,986.

U.S. Pat. Nos. 5,446,170 and 5,426,225 disclose that 2-aryl-5-(trifluoromethyl)pyrrole compounds may be obtained in four steps from the appropriate aldehyde. The processes described in those patents require the use of an aminonitrile intermediate which is obtained via the Strecker synthesis from the appropriate aldehyde. However, the use of the Strecker synthesis is not entirely satisfactory because of cyanide containing waste streams.

Accordingly, what is needed in the art is an efficient process for the preparation of 2-aryl-5-(perfluoroalkyl) pyrrole compounds which does not require the use of N-(substituted benzyl)-2,2,2-trifluoroacetimidoyl chloride compounds and avoids the use of the Strecker synthesis.

SUMMARY OF THE INVENTION

The present invention provides an efficient process for the preparation of 2-aryl-5-(perfluoroalkyl)pyrrole compounds having the structural formula I

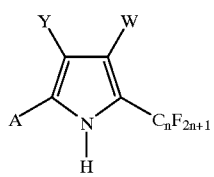

(I)

wherein
W is hydrogen or $C_mF_{2m+1}$;
Y is CN, $NO_2$ or $CO_2R$;
R is $C_1$–$C_4$alkyl;
m and n are each independently an integer of 1, 2, 3, 4, 5, 6, 7 or 8;

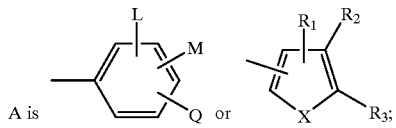

L is hydrogen or halogen;
M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfinyl, $C_1$–$C_4$haloalkylsulfinyl, $C_1$–$C_4$alkylsulfonyl, $C_1$–$C_4$haloalkylsulfonyl or when M and Q are on adjacent positions they may be taken together with the carbon atoms to which they are attached to form a ring in which MQ represents the structure —$OCH_2O$—, —$OCF_2O$— or —CH=CH—CH=CH—;
$R_1$, $R_2$ and $R_3$ are each independently hydrogen, halogen, $NO_2$, CHO or $R_2$ and $R_3$ may be taken together with the atoms to which they are attached to form a ring in which $R_2R_3$ is represented by the structure

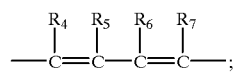

$R_4$, $R_5$, $R_6$ and $R_7$ are each independently hydrogen, halogen, CN or $NO_2$; and
X is O or S
which process comprises reacting an N-(perfluoroalkylmethyl)arylimidoyl chloride compound having the structural formula II

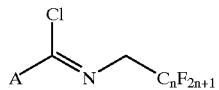

(II)

wherein A and n are as described above with a dieneophile compound having the structural formula III

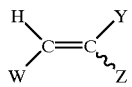

(III)

wherein W and Y are as described above and Z is Cl, Br or I, and a base in the presence of a solvent.

Advantageously, the process of this invention does not require the use of an N-(substituted benzyl)-2,2,2-trifluoroacetimidoyl chloride compound and avoids the use of the Strecker synthesis.

The present invention further provides novel N-(perfluoroalkylmethyl)arylimidoyl chloride compounds having the structural formula II

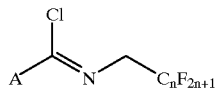

(II)

wherein n and A are as described hereinabove, provided that when A is unsubstituted phenyl, p-chlorophenyl or p-methylphenyl, n is an integer other than 1.

DETAILED DESCRIPTION OF THE INVENTION

The process of the present invention preferably comprises reacting an N-(perfluoroalkylmethyl)arylimidoyl chloride compound of formula II with at least about one molar equivalent, preferably about one to four molar equivalents, of a dienophile compound of formula III, and at least about one molar equivalent, preferably about one to four molar equivalents, of a base in the presence of a solvent preferably at a temperature range of about 5° C. to 100° C. to form 2-aryl-5-(perfluoroalkyl)pyrrole compounds of formula I.

Alternatively, the formula I compounds may be prepared by forming the formula III dienophile compounds in situ. This process comprises reacting an N-(perfluoroalkylmethyl)arylimidoyl chloride compound of formula II with preferably about one to four molar equivalents of an α,β-dihalo compound having the structural formula IV

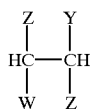

(IV)

wherein W and Y are as described hereinabove and Z is Cl, Br or I, and at least about two molar equivalents, prefereably about two to five molar equivalents, of a base in the presence of a solvent preferably at a temperature range of about 5° C. to 100° C. to form 2-aryl-5-(perfluoroalkyl)pyrrole compounds of formula I.

Advantageously, the present invention provides an efficient process for the preparation of 2-aryl-5-(perfluoroalkyl)pyrrole compounds which does not require the use of N-(substituted benzyl)-2,2,2-trifluoroacetimidoyl chloride compounds and avoids the use of the Strecker synthesis.

Suprisingly, it has been found that the N-(perfluoroalkylmethyl)arylimidoyl chloride compounds of this invention undergo cycloaddition reactions with dienophiles such as 2-chloroacrylonitrile to produce the same regioisomeric pyrrole compounds that are obtained by reacting the isomeric N-(substituted benzyl)-2,2,2-trifluoroacetimidoyl chloride compounds with dienophiles as described in U.S. Pat. No. 5,145,986. This novel, regiochemical outcome of the pyrrole forming reaction of the present invention thus provides alternative and potentially more economical ways to produce 2-aryl-5-(perfluoroalkyl)pyrrole compounds. In particular, the present invention provides an efficient process for the preparation of 2-aryl-5-(perfluoroalkyl)pyrrole compounds from acid halide compounds which are conveniently available starting materials.

A further advantage of the present invention is that a wider variety of the 2-aryl-5-(perfluoroalkyl)pyrrole compounds of formula I may be prepared from commercially available acid halide compounds. In contrast, although the process described in U.S. Pat. No. 5,145,986 produces 2-aryl-5-(trifluoromethyl)pyrrole compounds from N-(substituted benzyl)-2,2,2-trifluoroacetimidoyl chloride compounds, certain 2-aryl-5-(trifluoromethyl)pyrrole compounds would require benzoyl halide starting materials because of a lack of commercially available alternative starting materials. Therefore the present invention provides an improved process for those formula I pyrroles compounds.

For example, when the common starting material for the processes of this invention and U.S. Pat. No. 5,145,986 is limited to substituted benzoyl halide compounds due to economic factors including, but not limited to, commercial availability on a manufacturing scale, the process of the present invention is significantly more efficient for the preparation of the desired pyrrole compounds as shown below in Flow Diagram I.

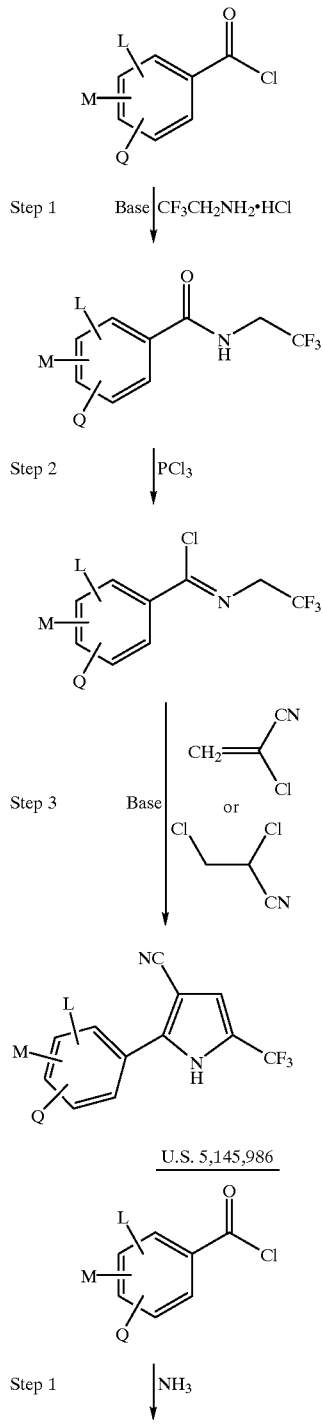

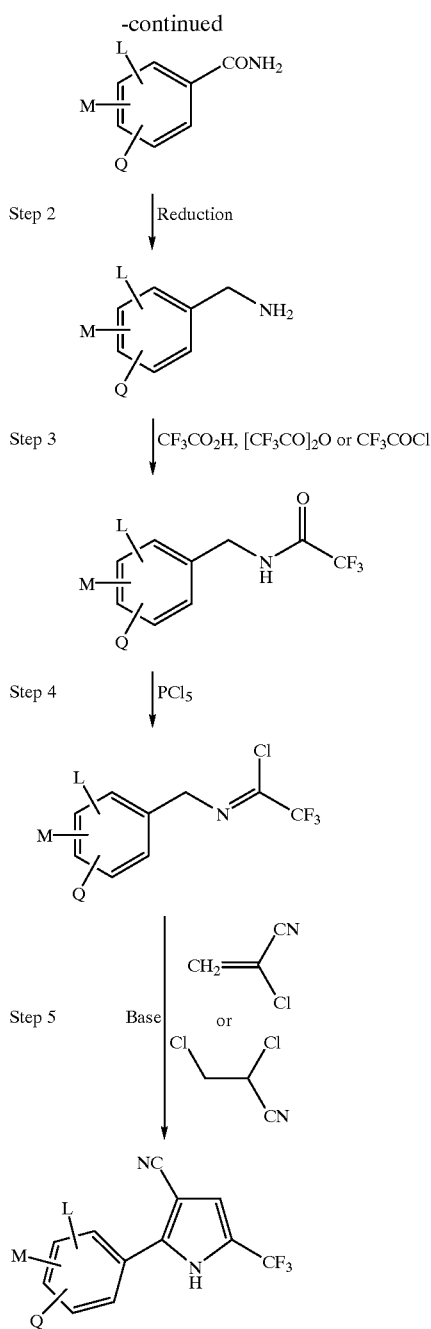

The formula I compounds of this invention may be isolated by conventional procedures such as dilution of the reaction mixture with water and filtration or, alternatively, extraction with a suitable solvent. Suitable extraction solvents include water-immiscible solvents such as ether, ethyl acetate, toluene, methylene chloride and the like.

Bases suitable for use in this invention include tri-($C_1$–$C_6$alkyl)amines such as trimethylamine, triethylamine, tripropylamine, tributylamine, diisopropylethylamine and the like; alkali metal carbonates such as potassium carbonate and sodium carbonate; alkali metal hydroxides such as potassium hydroxide and sodium hydroxide; alkali metal acetates such as potassium acetate and sodium acetate; and heterocyclic tertiary amines including, but not limited to, 1,8-diazabicyclo[5.4.0]undec-7-ene (DBU); 1,5-diazabicyclo[4.3.0]non-5-ene (DBN); 1,4-diazabicyclo-[2.2.2]octane; pyridine; substituted pyridines such as 2,6-dimethylpyridine, 2-methylpyridine, 3-methylpyridine, 4-methylpyridine and the like; quinoline; and substituted quinolines. Preferred bases include tri-($C_1$–$C_6$alkyl)-amines, 1,8-diazabicyclo[5.4.0]undec-7-ene, 1,5-diazabicyclo[4.3.0]non-5-ene, 1,4-diazabicyclo-[2.2.2]octane, potassium carbonate and sodium carbonate.

Solvents suitable for use in the present invention include, but are not limited to, carboxylic acid amides such as N,N-dimethylformamide, N,N-dimethylacetamide and the like; N-substituted pyrrolidinones such as N-methylpyrrolidinone and the like; nitriles such as acetonitrile, propionitrile and the like; halogenated hydrocarbons such as methylene chloride, chloroform, carbon tetrachloride and the like; ethers such as tetrahydrofuran, dioxane and the like; sulfoxides such as dimethyl sulfoxide and the like; and mixtures thereof. Preferred solvents include carboxylic acid amides and nitriles and mixtures thereof. N,N-dimethylformamide and acetonitrile and mixtures thereof are especially suitable for use in the present invention.

Exemplary of halogen hereinabove are fluorine, chlorine, bromine and iodine. The terms "$C_1$–$C_4$haloalkyl", "$C_1$–$C_4$haloalkoxy", "$C_1$–$C_4$haloalkylthio", "$C_1$–$C_4$haloalkylsulfinyl" and "$C_1$–$C_4$haloalkylsulfonyl", are defined as a $C_1$–$C_4$alkyl, $C_1$–$C_4$alkoxy, $C_1$–$C_4$alkylthio, $C_1$–$C_4$alkylsulfinyl or $C_1$–$C_4$alkylsulfonyl group substituted with one or more halogen atoms, respectively.

The present invention is especially useful for the preparation of formula I compounds wherein W is hydrogen;
Y is CN;
n is 1 or 2

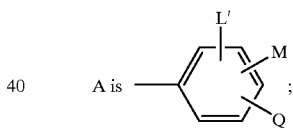

L is hydrogen or halogen; and
M and Q are each independently hydrogen, halogen, $C_1$–$C_4$haloalkyl or $C_1$–$C_4$haloalkoxy.

In particular, the present invention is useful for the preparation of
2-(4-chlorophenyl)-5-(trifluoromethyl)pyrrole-3-carbonitrile;
2-(3,5-dichlorophenyl)-5-(trifluoromethyl)pyrrole-3-carbonitrile;
2-(3,4-dichlorophenyl)-5-(trifluoromethyl)pyrrole-3-carbonitrile; and
2-(4-bromophenyl)-5-(trifluoromethyl)pyrrole-3-carbonitrile, among others.

The present invention also relates to novel N-(perfluoroalkylmethyl)arylimidoyl chloride compounds having the structural formula II (II)

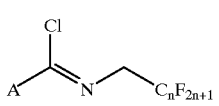

wherein
n is an integer of 1, 2, 3, 4, 5, 6, 7 or 8;

A is 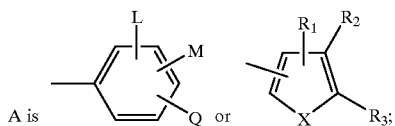 or

L is hydrogen or halogen;
M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$haloalkylthio, C$_1$–C$_4$alkylsulfinyl, C$_1$–C$_4$haloalkylsulfinyl, C$_1$–C$_4$alkylsulfonyl, C$_1$–C$_4$haloalkylsulfonyl or when M and Q are on adjacent positions they may be taken together with the carbon atoms to which they are attached to form a ring in which MQ represents the structure —OCH$_2$O—, —OCF$_2$O— or —CH=CH—CH=CH—;
R$_1$, R$_2$ and R$_3$ are each independently hydrogen, halogen, NO$_2$, CHO or R$_2$ and R$_3$ may be taken together with the atoms to which they are attached to form a ring in which R$_2$R$_3$ is represented by the structure

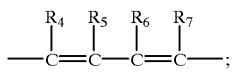

R$_4$, R$_5$, R$_6$ and R$_7$ are each independently hydrogen, halogen, CN or NO$_2$; and
X is O or S,
provided that when A is unsubstituted phenyl, p-chlorophenyl or p-methylphenyl, n is an integer other than 1.

Preferred novel formula II compounds of this invention are those wherein
n is 1 or 2;

A is 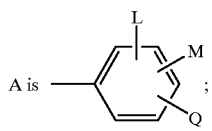;

L is hydrogen or halogen; and
M and Q are each independently hydrogen, halogen, C$_1$–C$_4$haloalkyl or C$_1$–C$_4$haloalkoxy,
provided that when A is unsubstituted phenyl or p-chlorophenyl, n is 2.

Novel formula II compounds which are particularly useful in the processes of this invention include
N-(2,2,2-trifluoroethyl)-3,5-dichlorobenzimidoyl chloride;
N-(2,2,2-trifluoroethyl)-3,4-dichlorobenzimidoyl chloride; and
N-(2,2,2-trifluoroethyl)-4-bromobenzimidoyl chloride, among others.

Starting formula II N-(perfluoroalkylmethyl)arylimidoyl chloride compounds may be prepared, as illustrated in Flow Diagram II, by reacting an acid halide compound having the structural formula V with a per-fluoroalkylmethylamine or perfluoroalkylmethylamine acid addition salt having the structural formula VI in the presence of a base to form a benzamide compound having the structural formula VII, and reacting the benzamide compound with (1) phosphorus pentachloride or (2) phosgene followed by N,N-dimethylformamide (DMF).

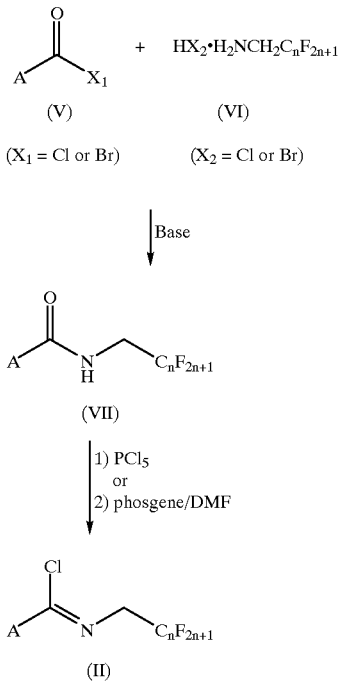

Alternatively, N-(perfluoroalkylmethyl)arylimidoyl chloride compounds of formula II may be prepared, as shown in Flow Diagram III, by isomerizing an N-(arylmethyl)perfluoroalkylformimidoyl chloride compound with a tertiary amine such as triethylamine at an elevated temperature according to the procedures described in Chemistry Letters, pp. 1463–1464 (1983). The N-(arylmethyl)perfluoroalkylformimidoyl chloride compounds may be prepared according to the procedures described in U.S. Pat. No. 5,145,986 and Chemistry Letters, pp. 1463–1464 (1983).

FLOW DIAGRAM III

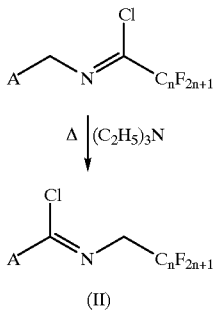

Starting formula III dienophile compounds are known in the art and may be prepared using conventional procedures. Compounds of formulas III and IV wherein W is C$_m$F$_{2m+1}$ may be prepared according to the procedures described in U.S. Pat. No. 5,068,390.

The formula I compounds are useful for the control of insect and acarid pests. In addition, the formula I compounds may be used to prepare other arylpyrrole insecticidal and acaridal agents having the structural formula VIII

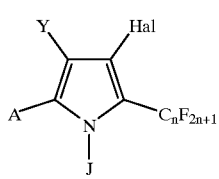

(VIII)

wherein

Y is CN, NO$_2$ or CO$_2$R;

R is C$_1$–C$_4$alkyl;

n is an integer of 1, 2, 3, 4, 5, 6, 7 or 8;

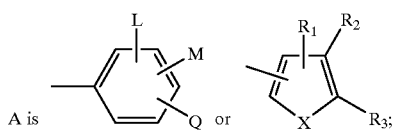

L is hydrogen or halogen;

M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$haloalkylthio, C$_1$–C$_4$alkylsulfinyl, C$_1$–C$_4$haloalkylsulfinyl, C$_1$–C$_4$alkylsulfonyl, C$_1$–C$_4$haloalkylsulfonyl or when M and Q are on adjacent positions they may be taken together with the carbon atoms to which they are attached to form a ring in which MQ represents the structure —OCH$_2$O—, —OCF$_2$O— or —CH=CH—CH=CH—;

R$_1$, R$_2$ and R$_3$ are each independently hydrogen, halogen, NO$_2$, CHO or R$_2$ and R$_3$ may be taken together with the atoms to which they are attached to form a ring in which R$_2$R$_3$ is represented by the structure

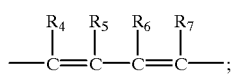

R$_4$, R$_5$, R$_6$ and R$_7$ are each independently hydrogen, halogen,

CN or NO$_2$;

X is O or S;

Hal is a halogen atom; and

J is hydrogen or C$_1$–C$_6$alkoxymethyl.

Advantageously, formula VIII arylpyrrole compounds may be prepared by a process which comprises:

(a) reacting an N-(perfluoroalkylmethyl)arylimidoyl chloride compound of formula II with a dienophile compound having the structural formula IX

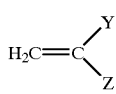

(IX)

wherein Y is as described above and Z is Cl, Br or I, and a base in the presence of a solvent to form a 2-aryl-5-(perfluoroalkyl)pyrrole compound having the structural formula X

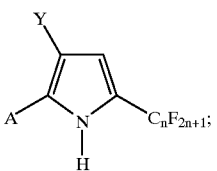

(X)

(b) halogenating the formula X compound to form the arylpyrrole compound of formula VIII wherein J is hydrogen; and (c) optionally alkoxymethylating the formula VIII compound wherein J is hydrogen to form the formula VIII arylpyrrole compound wherein J is C$_1$–C$_6$alkoxymethyl.

Alternatively, arylpyrrole compounds of formula VIII may be prepared by a process which comprises:

(a) reacting an N-(perfluoroalkylmethyl)arylimidoyl chloride compound of formula II with an α,β-dihalo compound having the structural formula XI

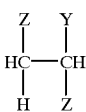

(XI)

wherein Y is as described above and Z is Cl, Br or I, and at least about two molar equivalents of a base in the presence of a solvent to form a 2-aryl-5-(perfluoroalkyl)pyrrole compound having the structural formula X

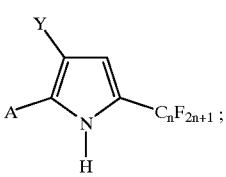

(X)

(b) halogenating the formula X compound to form the arylpyrrole compound of formula VIII wherein J is hydrogen; and (c) optionally alkyoxymethylating the formula VIII compound wherein J is hydrogen to form the formula VIII arylpyrrole compound wherein J is C$_1$–C$_6$alkoxymethyl.

The present invention is especially useful for the preparation of arylpyrrole compounds of formula VIII wherein Y is CN;

n is 1 or 2;

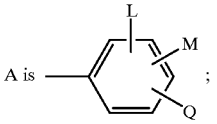

L is hydrogen or halogen;

M and Q are each independently hydrogen, halogen, C$_1$–C$_4$haloalkyl or C$_1$–C$_4$haloalkoxy;

Hal is Br or Cl; and

J is hydrogen or ethoxymethyl.

Halogenation methods may be any known methods such as those described in U.S. Pat. Nos. 5,010,098 and 5,449,789.

Alkoxymethylation procedures suitable for use in this invention include conventional procedures known in the art (see, e.g., U.S. Pat. Nos. 5,010,098 and 5,359,090). In a preferred embodiment of this invention, the alkoxymethylation procedure comprises reacting a formula VIII compound wherein J is hydrogen with a di-($C_1$–$C_6$alkoxy) methane compound, N,N-dimethylformamide and phosphorous oxychloride in the presence of an aprotic solvent to form a reaction mixture and treating the reaction mixture with a tertiary amine.

In order to facilitate a further understanding of this invention, the following examples are presented primarily for the purpose of illustrating more specific details thereof. The scope of the invention should not be deemed limited by the examples, but encompasses the entire subject matter defined in the claims.

EXAMPLE 1

Preparation of N-(2,2,2-Trifluoroethyl)-4-chlorobenzamide Using Triethylamine as the Base

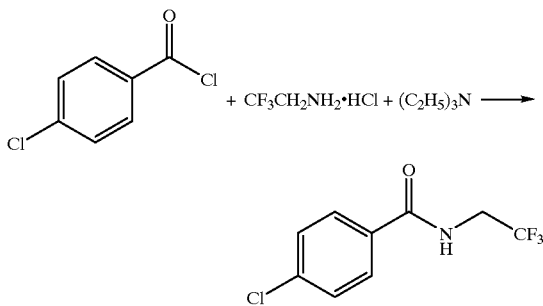

A mixture of 4-chlorobenzoyl chloride (64.6 g, 0.37 mol) and 2,2,2-trifluoroethylamine hydrochloride (50.0 g, 0.37 mol) in toluene is treated with triethylamine (80.9 g, 0.8 mol) at such a rate that the temperature is kept below 40° C. The reaction mixture is stirred overnight at room temperature and diluted with water and ethyl acetate. The organic layer is separated, washed with water and concentrated in vacuo to obtain a residue. The residue is crystallized from heptane to give the title product as a white solid (71.9 g, 81.7% yield, mp 108–111° C.) which is identified by $^1$H and $^{19}$F NMR.

Using essentially the same procedure, but using the appropriately substituted benzoyl chloride, the following compounds are obtained:

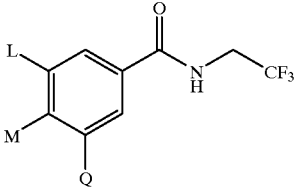

| L | M | Q | mp ° C. | % Yield |
| --- | --- | --- | --- | --- |
| H | Br | H | 120–121 | 79.1 |
| H | Cl | Cl | 128–135 | 91.2 |
| Cl | H | Cl | 145–147 | 83.7 |

EXAMPLE 2

Preparation of N-(2,2,2-Trifluoroethyl)-4-chlorobenzamide Using Sodium Carbonate as the Base

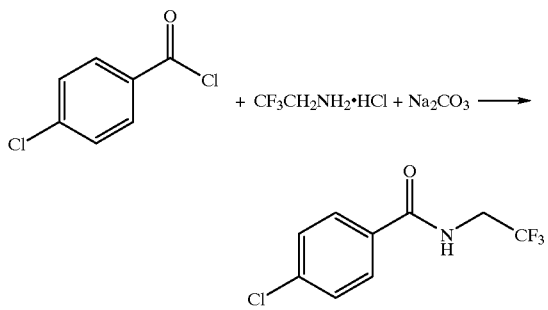

A mixture of 2,2,2-trifluoroethylamine hydrochloride (100.0 g, 0.74 mol) and sodium carbonate (169.4 g, 1.6 mol) in a 1:1 toluene and water mixture is treated with 4-chlorobenzoyl chloride (129.2 g, 0.74 mol) over 30 minutes as the temperature rises to 38° C., stirred for one hour, and diluted with ethyl acetate and water. The aqueous phase is separated and extracted with ethyl acetate. The organic phases are combined, washed with water, concentrated in vacuo and treated with heptane. The crystalline solids are filtered and dried to give the title product as a white solid (175.8 g, 100% yield, mp 108.5–112° C.).

Using essentially the same procedure, but substituting 3,5-dichlorobenzoyl chloride for 4-chlorobenzoyl chloride, N-(2,2,2-trifluoroethyl)-3,5-dichlorobenzamide is obtained as a white solid, mp 145–147° C., 95.5% yield.

EXAMPLE 3

Preparation of N-(2,2,2-Trifluoroethyl)-4-chlorobenzimidoyl Chloride Using Phosphorus Pentachloride

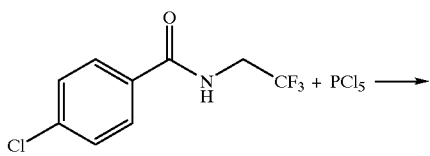

-continued

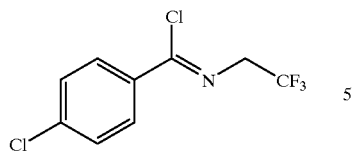

A mixture of N-(2,2,2-trifluoroethyl)-4-chlorobenzamide (65.0 g, 0.274 mol) and phosphorus pentachloride (57.0 g, 0.274 mol) is heated to and held at 100° C. for 2 hours. After the phosphorus oxychloride is removed at a slightly lower vacuum, the title product is vacuum distilled and collected as a colorless liquid (68.0 g, 96.9% yield, bp 91–92° C./1.3 mmHg) which is identified by $^1$H and $^{19}$F NMR.

Using essentially the same procedure, but using the appropriately substituted benzamide, the following compounds are obtained:

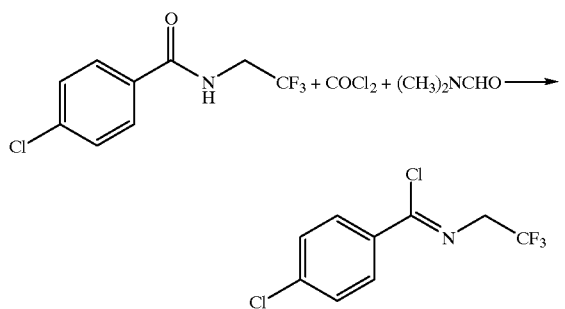

| L | M | Q | bp/mmHg | % Yield |
|---|---|---|---------|---------|
| H | Br | H | 88–90/0.5 | 93.3 |
| H | Cl | Cl | 108–110/0.5 | 95.4 |
| Cl | H | Cl | 101–103/0.5 | 90.7 |

EXAMPLE 4

Preparation of N-(2,2,2-Trifluoroethyl)-4-chlorobenzimidoyl Chloride Using Phosgene and N,N-dimethylformamide

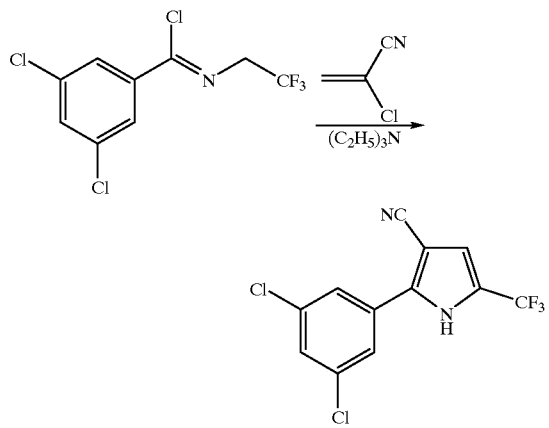

A mixture of N-(2,2,2-trifluoroethyl)-4-chlorobenzamide (88.4 g, 0.37 mol) in a solution of phosgene in toluene (366.0 g as 20% solution, 0.74 mol) is treated with N,N-dimethylformamide (54.0 g, 0.74 mol) over 45 minutes as the temperature rises to 50° C. The reaction mixture is then heated to and held at 100° C. for 4 hours. The toluene layer is separated and concentrated in vacuo to obtain a residue. The residue is vacuum distilled to give the title product as a colorless oil (80.0 g, 84.5% yield, bp 81–83° C./0.4 mmHg)

Using essentially the same procedure, but substituting N-(2,2,2-trifluoroethyl)-3,5-dichlorobenzamide for N-(2,2,2-trifluoroethyl)-4-chlorobenzamide, N-(2,2,2-trifluoroethyl)-3,5-dichlorobenzimidoyl chloride is obtained as a colorless liquid, 62% yield.

EXAMPLE 5

Preparation of 2-(3,5-Dichlorophenyl)-5-(trifluoromethyl)pyrrole-3-carbonitrile Using 2-chloroacrylonitrile A solution of N-(2,2,2-Trifluoroethyl)-3,5-dichlorobenzimidoyl chloride (8.72 g, 0.03 mol) in N,N-dimethylformamide is treated with 2-chloroacrylonitrile (3.0 g, 0.0345 mol) under a nitrogen atmosphere. Triethylamine (9.56 g, 0.0945 mol) is added slowly at 50° C. over three hours and the reaction mixture is stirred at 50° C. for 17 hours. The reaction mixture is then quenched with water and extracted with methylene chloride. The organic layer is washed with water and concentrated in vacuo to obtain a brown solid. Flash column chromatography of the brown solid using silica gel and a 15% ethyl acetate in heptane solution gives the title product as a pale yellow solid (7.4 g, 80.9% yield).

Following essentially the same procedure, but using the appropriately substituted benzimidoyl chloride and substituting 1,8-diazabicyclo[5.4.0]undec-7-ene (DBU) for triethylamine, the following compounds are obtained:

| L | M | Q | mp ° C. | % Yield |
|---|---|---|---------|---------|
| Cl | H | Cl | | 87.4 |
| H | Br | H | 247.5–248.5 | 70.9 |
| H | Cl | Cl | | 87.4 |
| H | Cl | H | | 39.4 |

EXAMPLE 6

Preparation of 2-(3,5-Dichlorophenyl)-5-(trifluoromethyl)pyrrole-3-carbonitrile Using 2,3-dichloropropionitrile

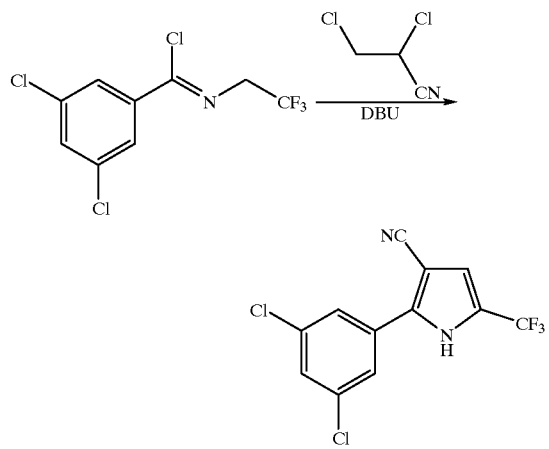

A solution of N-(2,2,2-trifluoroethyl)-3,5-dichlorobenzimidoyl chloride (8.72 g, 0.03 mol) in N,N-dimethylformamide is treated with 2,3-dichloropropionitrile (4.3 g, 0.0345 mol) under a nitrogen atmosphere. 1,8-diazabicyclo-[5.4.0]undec-7-ene (DBU, 15.2 g, 0.10 mol) is added over one hour at such a rate that the reaction mixture temperature is kept at 50° C. The reaction mixture is then held at 45° C. for 2 hours and slowly quenched with aqueous HCl at 25° C. The brown solids are filtered, washed with water, and dried in a vacuum oven at 60° C. to give the title product as a brown solid (8.64 g, 94.4% yield) which is identified by $^{19}F$ and $^1H$ NMR.

EXAMPLE 7

Preparation of Methyl 2-(p-chlorophenyl)-5-(trifluoromethyl)pyrrole-3-carboxylate

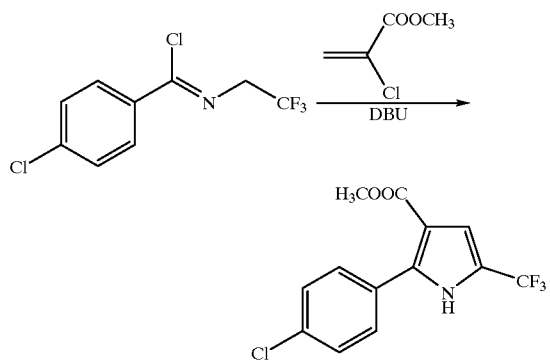

A solution of N-(2,2,2-trifluoroethyl)-4-chlorobenzimidoyl chloride (10.2 g, 0.04 mol) and methyl 2-chloroacrylate (5.8 g, 0.048 mol) in N,N-dimethylformamide is treated with 1,8-diazabicyclo[5.4.0]undec-7-ene (DBU, 19.5 g, 0.128 mol) over 30 minutes at such a rate that the temperature is kept at 40° C., stirred for two hours, and quenched with water and ethyl acetate. The organic layer is separated, washed sequentially with aqueous HCl and water, and concentrated in vacuo to obtain an oil. Flash column chromatography of the oil using silica gel and a 20% ethyl acetate in heptane solution and crystallization from heptane gives the title product as white crystals (4.2 g, 34.6% yield, mp 120.0–122.5° C.)

EXAMPLE 8

Preparation of 4-Bromo-2-(3,5-dichlorophenyl)-5-(trifluoromethyl)pyrrole-3-carbonitrile

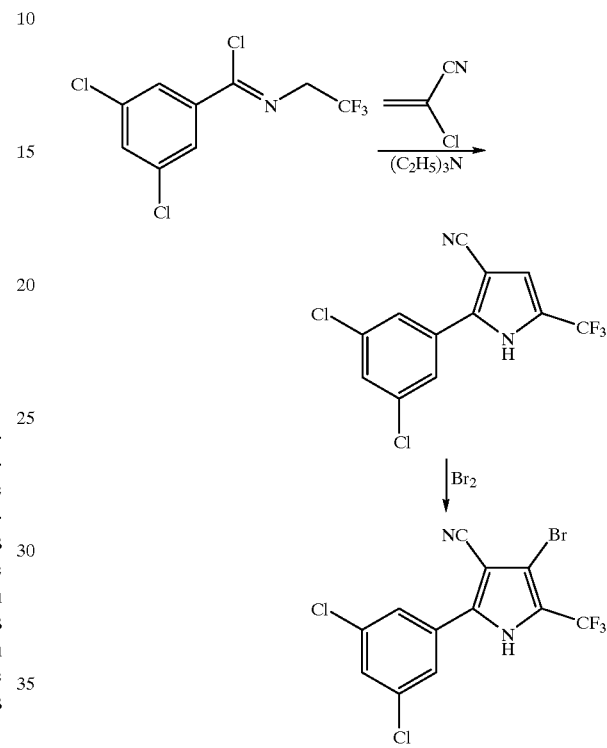

A solution of N-(2,2,2-trifluoroethyl)-3,5-dichlorobenzimidoyl chloride (8.72 g, 0.03 mol) in N,N-dimethylformamide is treated with 2-chloroacrylonitrile (3.0 g, 0.0345 mol) under a nitrogen atmosphere. Triethylamine (9.56 g, 0.0945 mol) is added slowly at 50° C. over two hours and the reaction mixture is stirred at 58°–60° C. for 18 hours. Bromine (4.8 g, 0.03 mol) is then added over 20 minutes as the temperature rises from 25° C. to 36° C. The resultant reaction mixture is diluted with water and extracted with methylene chloride. Evaporation and flash column chromatography using silica gel and a 20% ethyl acetate in heptane solution gives the title product as a white crystalline solid (5.4 g, 46.9% yield) which is identified by $^{19}F$ and $^1H$ NMR.

I claim:

1. A process for the preparation of an arylpyrrole compound having the structural formula VIII

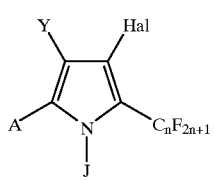

(VIII)

wherein

Y is CN, NO$_2$ or CO$_2$R;

R is C$_1$–C$_4$alkyl;

n is an integer of 1, 2, 3, 4, 5, 6, 7 or 8;

A is 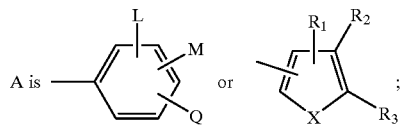

L is hydrogen or halogen;

M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$haloalkylthio, C$_1$–C$_4$alkylsulfinyl, C$_1$–C$_4$haloalkylsulfinyl, C$_1$–C$_4$alkylsulfonyl, C$_1$–C$_4$haloalkylsulfonyl or when M and Q are on adjacent positions they may be taken together with the carbon atoms to which they are attached to form a ring in which MQ represents the structure —OCH$_2$O—, —OCF$_2$O— or —CH=CH—CH=CH—;

R$_1$, R$_2$ and R$_3$ are each independently hydrogen, halogen, NO$_2$, CHO or R$_2$ and R$_3$ may be taken together with the atoms to which they are attached to form a ring in which R$_2$R$_3$ is represented by the structure

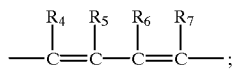

R$_4$, R$_5$, R$_6$ and R$_7$ are each independently hydrogen, halogen, CN or NO$_2$;

X is O or S;

Hal is a halogen atom; and

J is hydrogen or C$_1$–C$_6$alkoxymethyl which process comprises the steps of:

(a) reacting an N-(perfluoroalkylmethyl)arylimidoyl chloride compound having the structural formula II

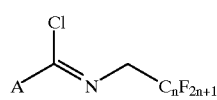

wherein A and n are as described above with a dieneophile compound having the structural formula IX

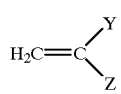

wherein Y is as described above and Z is Cl, Br or I, and a base in the presence of a solvent to form a 2-aryl-5-(perfluoroalkyl)pyrrole compound having the structural formula X

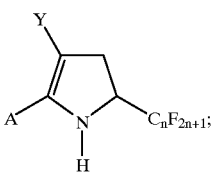

(b) halogenating the formula X compound to form the arylpyrrole compound of formula VIII wherein J is hydrogen; and (c) optionally alkoxymethylating the formula VIII compound wherein J is hydrogen.

2. The process according to claim 1 wherein step (c) comprises reacting the formula VIII compound wherein J is hydrogen with a di(C$_1$–C$_6$alkoxy)methane compound, N,N-dimethylformamide and phosphorous oxychloride in the presence of an aprotic solvent to form a reaction mixture and treating the reaction mixture with a tertiary amine.

3. A process for the preparation of an arylpyrrole compound having the structural formula VIII

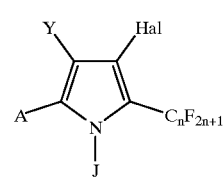

wherein

Y is CN, NO$_2$ or CO$_2$R;

R is C$_1$–C$_4$alkyl;

n is an integer of 1, 2, 3, 4, 5, 6, 7 or 8;

A is 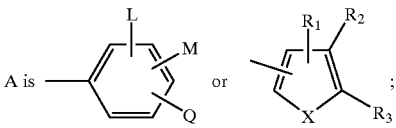

L is hydrogen or halogen;

M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$haloalkylthio, C$_1$–C$_4$alkylsulfinyl, C$_1$–C$_4$haloalkylsulfinyl, C$_1$–C$_4$alkylsulfonyl, C$_1$–C$_4$haloalkylsulfonyl or when M and Q are on adjacent positions they may be taken together with the carbon atoms to which they are attached to form a ring in which MQ represents the structure —OCH$_2$O—, —OCF$_2$O— or —CH=CH—CH=CH—;

R$_1$, R$_2$ and R$_3$ are each independently hydrogen, halogen, NO$_2$, CHO or R$_2$ and R$_3$ may be taken together with the atoms to which they are attached to form a ring in which R$_2$R$_3$ is represented by the structure

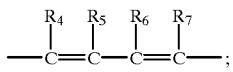

R$_4$, R$_5$, R$_6$ and R$_7$ are each independently hydrogen, halogen, CN or NO$_2$;

X is O or S;
Hal is a halogen atom; and
J is hydrogen or $C_1$–$C_6$alkoxymethyl
which process comprises the steps of:
(a) reacting an N-(perfluoroalkylmethyl)arylimidoyl chloride compound having the structural formula II

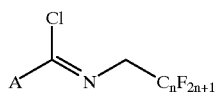
(II)

wherein A and n are as described above with an α,β-dihalo compound having the structural formula XI

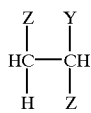
(XI)

wherein Y is as described above and Z is Cl, Br or I, and at least about two molar equivalents of a base in the presence of a solvent to form a 2-aryl-5-(perfluoroalkyl)pyrrole compound having the structural formula X

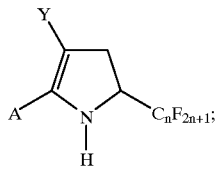
(X)

(b) halogenating the formula X compound to form the arylpyrrole compound of formula VIII wherein J is hydrogen; and
(c) optionally alkoxymethylating the formula VIII compound wherein J is hydrogen.

4. The process according to claim 3 wherein step (c) comprises reacting the formula VIII compound wherein J is hydrogen with a di($C_1$–$C_6$alkoxy)methane compound, N,N-dimethylformamide and phosphorous oxychloride in the presence of an aprotic solvent to form a reaction mixture and treating the reaction mixture with a tertiary amine.

* * * * *